US008600470B2

(12) United States Patent
Van Antwerp et al.

(10) Patent No.: US 8,600,470 B2
(45) Date of Patent: *Dec. 3, 2013

(54) METHOD FOR DETECTING AN ANALYTE IN BLOOD

(75) Inventors: Nannette M. Van Antwerp, Valencia, CA (US); Udo Hoss, Sherman Oaks, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 109 days.

This patent is subject to a terminal disclaimer.

(21) Appl. No.: 13/233,338

(22) Filed: Sep. 15, 2011

(65) Prior Publication Data
US 2012/0004524 A1   Jan. 5, 2012

Related U.S. Application Data

(63) Continuation of application No. 11/348,894, filed on Feb. 7, 2006, now Pat. No. 8,032,198, which is a continuation-in-part of application No. 10/935,954, filed on Sep. 8, 2004, now Pat. No. 7,468,033.

(51) Int. Cl.
*A61B 5/05*   (2006.01)
*A61B 5/00*   (2006.01)

(52) U.S. Cl.
USPC .......................................... 600/347; 600/365

(58) Field of Classification Search
USPC .......................................... 600/309, 345–366
See application file for complete search history.

(56) References Cited

U.S. PATENT DOCUMENTS

| | | |
|---|---|---|
| 3,986,508 A | 10/1976 | Barrington |
| 4,161,949 A | 7/1979 | Thanawalla |
| 4,403,984 A | 9/1983 | Ash et al. |
| 4,484,987 A | 11/1984 | Gough |
| 4,538,616 A | 9/1985 | Rogoff |
| 4,539,616 A * | 9/1985 | Yuito et al. ............... 360/123.19 |
| 4,610,469 A | 9/1986 | Wolff-Mooij |

(Continued)

FOREIGN PATENT DOCUMENTS

| | | |
|---|---|---|
| EP | 0354719 | 2/1990 |
| WO | 98/56293 | 12/1998 |

OTHER PUBLICATIONS

Gough et al. "Perspectives in diabetes, development of the implantable glucose sensor, what are the prospects and why is it taking so long?", Diabetes, vol. 44, pp. 1005-1009, Sep. 1995.

(Continued)

*Primary Examiner* — Navin Natnithithadha
(74) *Attorney, Agent, or Firm* — Gates & Cooper LLP

(57) ABSTRACT

The methods and apparatus for detecting an analyte in blood are useful for detecting an analyte in tissue of a subject. The apparatus comprises a sensor, which comprises an elongated conductive material having a protrudent end, the protrudent end comprising an electrode that detects the presence of an analyte; a substrate affixed to the conductive material; and a support having an external surface, a proximal end, and a distal end. The conductive material is positioned on the support and the protrudent end of the conductive material protrudes beyond the distal end of the support. Optionally, the sensor is suspended within the lumen of a venous flow device. Typically, only a portion of the sensor is suspended within the lumen of the venous flow device, said portion comprising the protrudent end of the conductive material. Alternatively, the conductive material is positioned on the external surface of the intravenous infusion catheter.

20 Claims, 12 Drawing Sheets

(56) References Cited

U.S. PATENT DOCUMENTS

| | | |
|---|---|---|
| 4,928,694 A | 5/1990 | Maxwell |
| 4,974,929 A | 12/1990 | Curry |
| 5,122,123 A | 6/1992 | Vaillancourt |
| 5,165,406 A | 11/1992 | Wong |
| 5,372,133 A | 12/1994 | Hogen Esch |
| 5,391,250 A | 2/1995 | Cheney et al. |
| 5,403,700 A | 4/1995 | Heller et al. |
| 5,536,262 A | 7/1996 | Velasquez |
| 5,569,186 A | 10/1996 | Lord et al. |
| 5,586,553 A | 12/1996 | Halili et al. |
| 5,651,767 A | 7/1997 | Schulman et al. |
| 5,914,026 A | 6/1999 | Blubaugh et al. |
| 5,976,085 A | 11/1999 | Kimball et al. |
| 6,091,975 A | 7/2000 | Daddona et al. |
| 6,099,485 A | 8/2000 | Patterson |
| 6,119,028 A | 9/2000 | Schulman et al. |
| 6,128,519 A | 10/2000 | Say |
| 6,134,461 A | 10/2000 | Say et al. |
| 6,175,752 B1 | 1/2001 | Say et al. |
| 6,484,045 B1 | 11/2002 | Holker et al. |
| 6,489,183 B1 | 12/2002 | Farnworth |
| 6,560,471 B1 | 5/2003 | Heller et al. |
| 6,916,294 B2 | 7/2005 | Ayad |
| 6,918,873 B1 | 7/2005 | Millar et al. |
| 8,032,198 B2 * | 10/2011 | Van Antwerp et al. ....... 600/347 |
| 2003/0130616 A1 | 7/2003 | Steil et al. |
| 2005/0054909 A1 | 3/2005 | Petisce et al. |
| 2005/0272989 A1 | 12/2005 | Shah et al. |
| 2006/0293576 A1 | 12/2006 | Van Atwerp et al. |

OTHER PUBLICATIONS

Monroe, "Novel implantable glucose sensors", ACL, pp. 8-16, Dec. 1989.

* cited by examiner

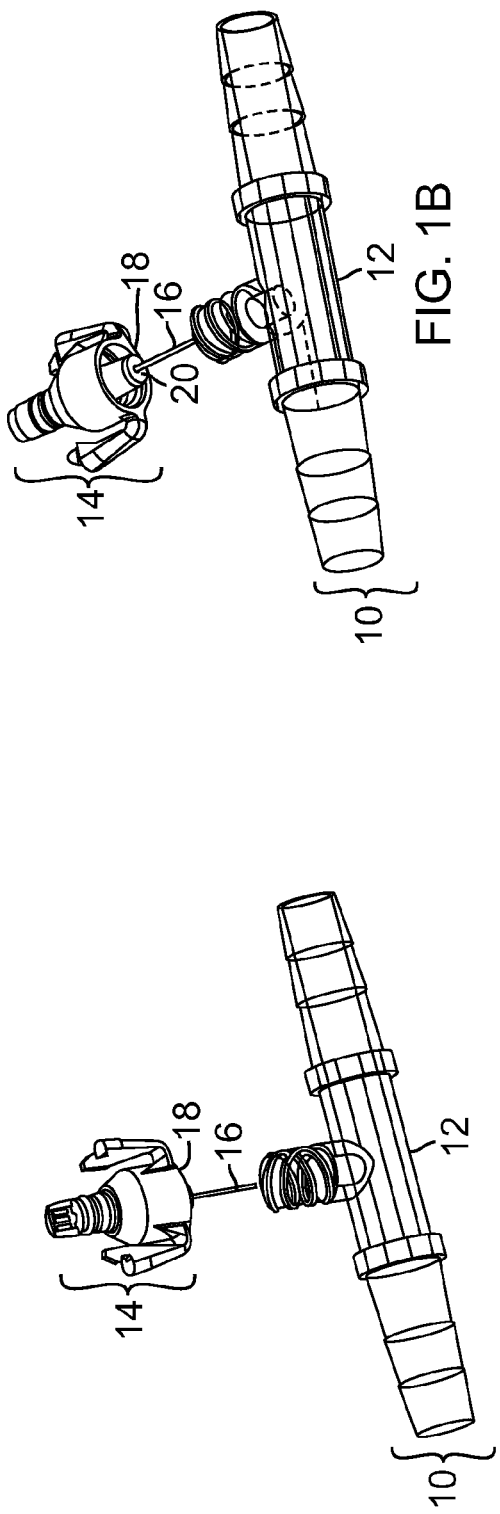
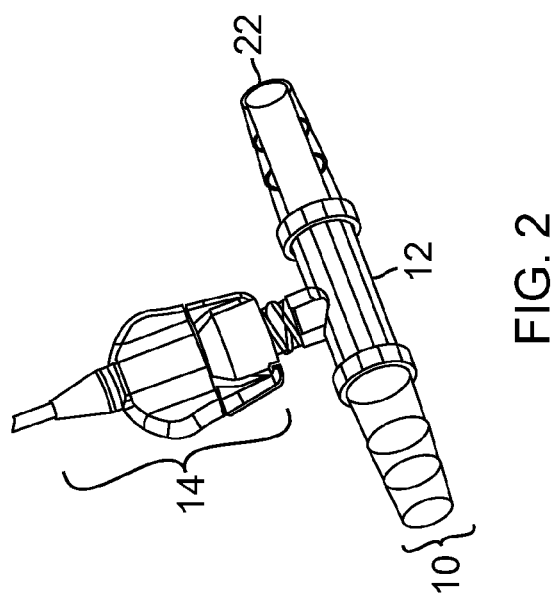

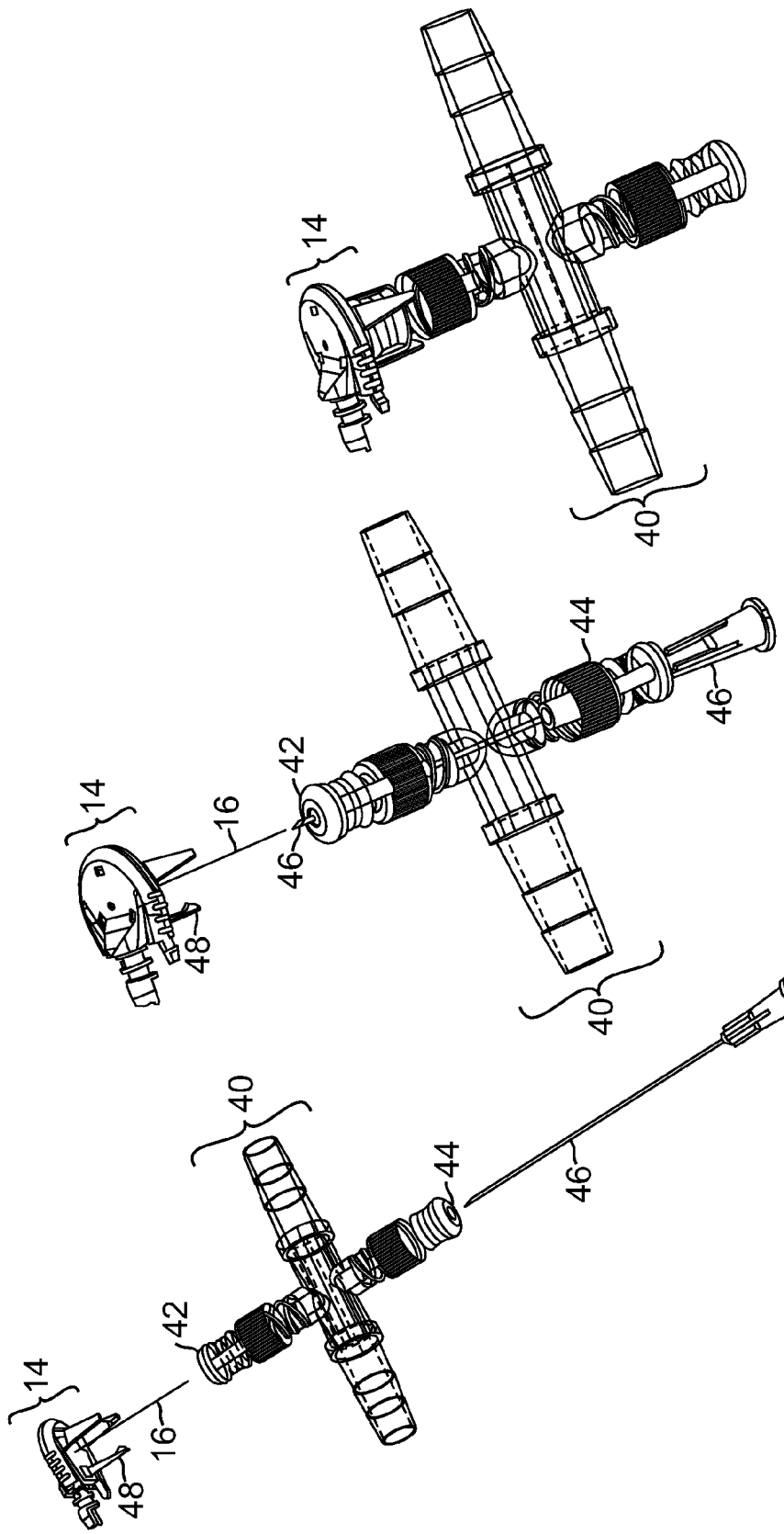

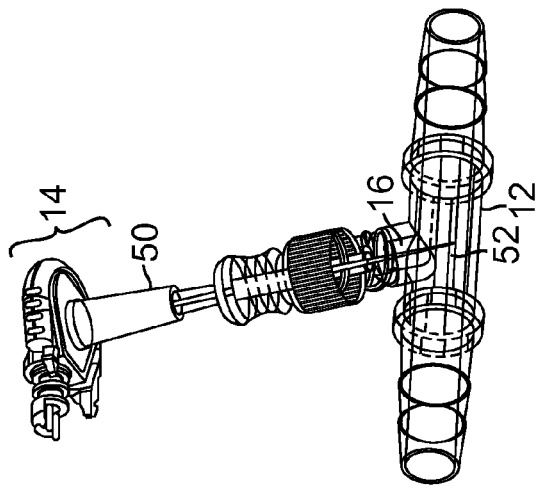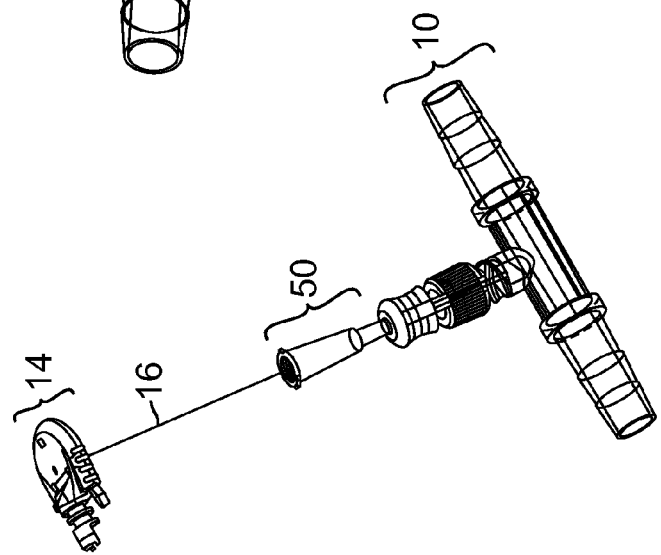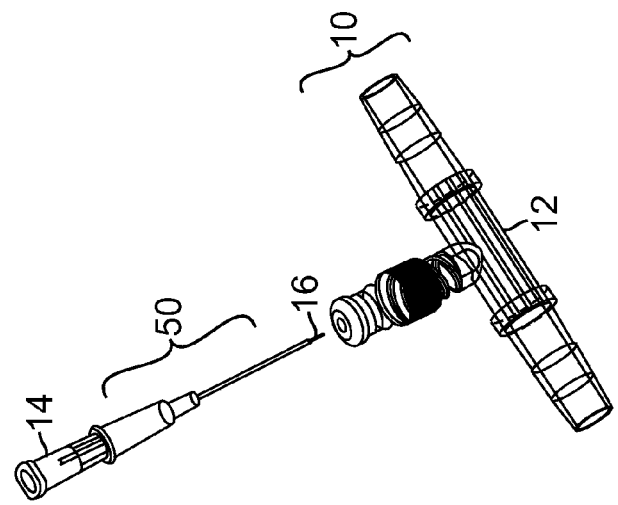

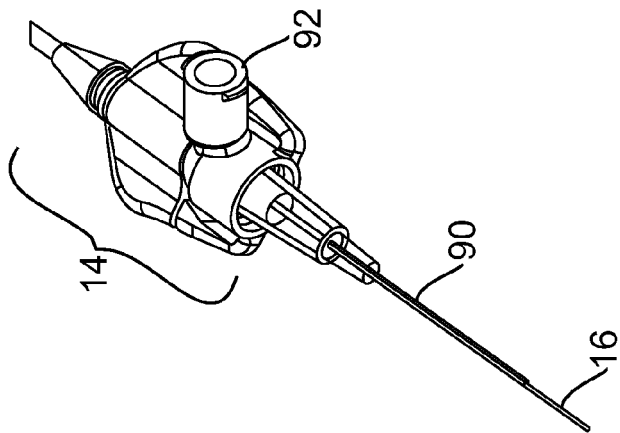
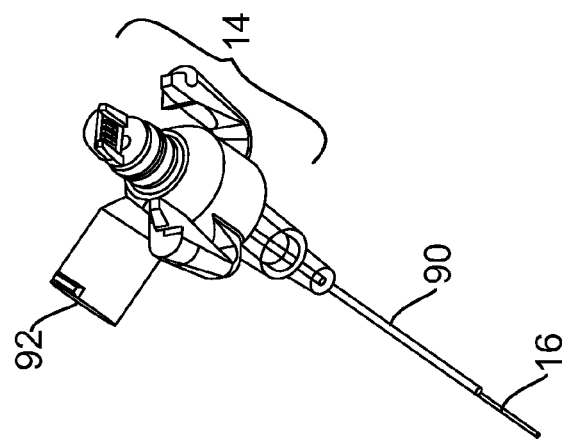
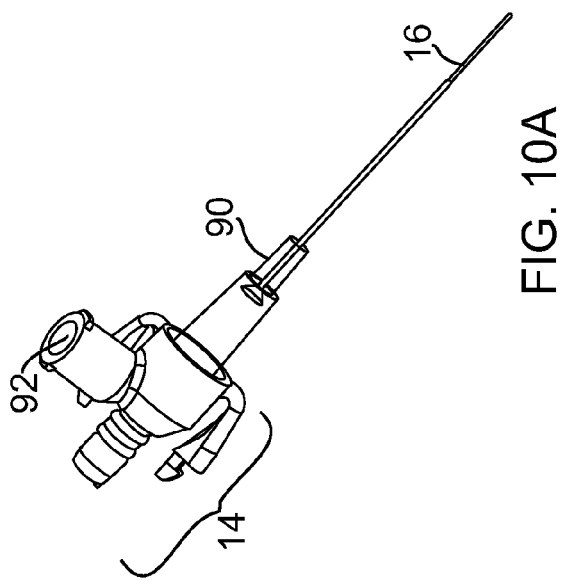

METHOD FOR DETECTING AN ANALYTE IN BLOOD

This application is a continuation of U.S. patent application Ser. No. 11/348,894, filed Feb. 7, 2006, which is a continuation-in-part of U.S. patent application Ser. No. 10/935,954, filed Sep. 8, 2004, now U.S. Pat. No. 7,468,033, issued Dec. 23, 2008, the entire contents of which are incorporated herein by reference.

TECHNICAL FIELD OF THE INVENTION

This invention relates generally to the manufacture and use of a sensor suitable for direct contact with blood, interstitial tissue or other medium. The sensor is capable of measuring glucose and/or other analytes, the design of the sensor facilitating introduction and use of the sensor in a variety of environments, including blood vessels, extracorporeal circuits, and interstitium.

BACKGROUND OF THE INVENTION

The assay of biochemical analytes such as glucose and lactate is important in a variety of clinical contexts. Biomedical sensors, such as enzyme electrodes, can be used to determine the concentration of certain biochemicals rapidly and with considerable accuracy. Enzyme electrodes can detect glucose, urea, uric acid, various alcohols, and a number of amino acids under certain well-defined conditions. For example, the monitoring of glucose concentrations in fluids of the human body is of particular relevance to diabetes management. Continuously or intermittently operating glucose sensors, including sensors implanted in the human body (such as the Continuous Glucose Monitoring System (CGMS) and Telemetered Glucose Monitoring System (TGMS) by Medtronic MiniMed), are sought for the management of diabetes, for example, for warning of imminent or actual hypoglycemia as well as its avoidance. The monitoring of lactate concentrations in fluids of the human body is useful in the diagnosis and assessment of a number of medical conditions including trauma, myocardial infarction, congestive heart failure, pulmonary edema and septicemia. For example, glucose sensors suitable for in vivo use can be prepared by depositing a glucose sensitive enzyme, such as glucose oxidase, onto an electrode via an electromotive plating process.

Biomedical measuring devices commonly used to monitor physiological variables include amperometric sensor devices that utilize electrodes modified with an appropriate enzyme coating. Sensors having such enzyme electrodes enable the user to determine the concentration of various analytes rapidly and with considerable accuracy, for example by utilizing the reaction of an enzyme and an analyte where this reaction utilizes a detectable coreactant and/or produces a detectable reaction product. For example, a number of glucose sensors have been developed that are based on the reaction between glucose and glucose oxidase (GOx). As glucose and oxygen diffuse into an immobilized enzyme layer on a sensor, the glucose reacts with oxygen and water to produce $H_2O_2$. Glucose can be detected electrochemically using the immobilized enzyme glucose oxidase coupled to oxygen and/or hydrogen peroxide-sensitive electrodes. The reaction results in a reduction in oxygen and the production of hydrogen peroxide proportional to the concentration of glucose in the sample medium. A typical device is composed of at least two detecting electrodes, or at least one detecting electrode and a reference signal source, to sense the concentration of oxygen or hydrogen peroxide in the presence and absence of enzyme reaction. Additionally, the complete monitoring system typically contains an electronic sensing and control means for determining the difference in the concentration of the substances of interest. From this difference, the concentration of analytes such as glucose can be determined.

A wide variety of such analyte sensors as well as methods for making and using such sensors are known in the art. Examples of such sensors, sensor sets and methods for their production are described, for example, in U.S. Pat. Nos. 5,390,691, 5,391, 250, 5,482,473, 5,299,571, 5,568,806 as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference. While a number of sensor designs and processes for making such sensors are known in the art, many are tailored to subcutaneous applications. There remains a need for the identification of the methods and processes that facilitate the measurement of glucose and other analytes in a variety of direct blood contacting applications. The present invention fulfills these needs and provides further related advantages.

SUMMARY OF THE INVENTION

To overcome the limitations in the prior art described above, and to overcome other limitations that will become apparent upon reading and understanding the present specification, embodiments of the invention provide methods and apparatus for detecting an analyte in blood. The invention provides an apparatus that comprises a sensor for detecting an analyte in tissue of a subject. The sensor comprises an elongated conductive material having a protrudent end, the protrudent end comprising an electrode that detects the presence of an analyte; a substrate affixed to the conductive material; and, optionally, a support having an external surface, a proximal end, and a distal end. The conductive material is positioned on the support and the protrudent end of the conductive material protrudes beyond the distal end of the support.

In one embodiment, the substrate comprises a polyimide film that is about 0.005 to about 0.007 inch in thickness. In this embodiment, the substrate is sufficiently supportive that a separate support element is not necessary. The entire sensor is therefore capable of protruding into the sensor environment where it can contact the analyte to be detected. The substrate optionally comprises an insulative layer that covers the conductive material and does not cover the electrode. In one embodiment, the apparatus further comprises an assembly means having a sensor end and an exterior face, wherein the sensor is affixed to the sensor end of the assembly means, and the assembly means is adapted for coupling with a venous flow device.

In a typical embodiment, the apparatus further comprises a venous flow device coupled to the assembly means, the venous flow device having a lumen, wherein the sensor is suspended within the lumen of the venous flow device. Optionally, only a portion of the sensor is suspended within the lumen of the venous flow device, said portion comprising the protrudent end of the conductive material.

In one embodiment, the support comprises an intravenous infusion catheter having a lumen. The intravenous catheter can have a single lumen or more than one lumen. The conductive material can be positioned on the external surface of the intravenous infusion catheter, and/or on the lumen of the intravenous infusion catheter.

In one embodiment, the venous flow device comprises an external blood loop. The external blood loop can optionally further comprise a septum adapted to receive injections.

Typically, the sensor comprises an enzymatic, molecular recognition, optochemical or electrochemical sensor, such as a glucose sensor.

The substrate can comprise a hydrophilic material. Examples of hydrophilic materials include, but are not limited to, polyurethane, acrylate, polyester and cross-linked PEO. In one embodiment, the sensor further comprises a coating.

In one embodiment, the distal end of the sensor is coated with a hydrophilic material. Typically, the distal end is dip-coated with the hydrophilic material. Alternatively, the coating can be applied by painting, spraying or other means known in the art. The sensor can be coated with a medicinal agent, such as an anticoagulant, or an antimicrobial agent. In one embodiment, the coating contains a hydrophilic polymer. Examples of hydrophilic polymers include, but are not limited to, polyhydroxyethylmethacrylate (PHEMA), polysaccharide, polyacrylamide, polyurea, polyethylene oxide (PEO) containing polyurethane, PEO containing polyurea and cross-linked PEO. Optionally, the coating comprises a stiffening agent.

The apparatus can comprise a sensor that detects the presence of an analyte and an assembly means. The assembly means has a sensor end, wherein the sensor end of the assembly means is affixed to the sensor, and the assembly means is adapted for coupling with a venous flow device. By coupling with a venous flow device, the assembly means brings the sensor into direct contact with blood flowing through the venous flow device.

In some embodiments, the apparatus further comprises a venous flow device coupled to the assembly means. The venous flow device has a lumen, and the sensor is positioned as desired, relative to the lumen of the venous flow device. In one embodiment, the sensor extends from within the lumen of the venous flow device beyond a distal end of the venous flow device. In another embodiment, the sensor is positioned external to the venous flow device and therefore does not pass through the lumen of the venous flow device. The venous flow device can be an intravenous catheter, such as a peripheral catheter, central catheter, or peripherally-inserted central catheter. In some embodiments, the venous flow device comprises an external blood loop, such as is used in extra-corporeal membrane oxygenation or hemodialysis. The venous flow device can have one or more lumens. Optionally, an opening is provided between the lumens. An inter-lumenal opening can permit the introduction of a medication, such as an anti-coagulant, into the area in which the sensor is suspended. Placement of the opening or openings can be designed to direct a medication or other agent to a particular portion or region of the sensor.

In some embodiments, the venous flow device further comprises a septum adapted to receive injections. For use with an external blood loop, the septum can be affixed to a T-connector, for example, so that a sensor apparatus can be introduced into the external blood loop through the septum. In another embodiment, the external blood loop further comprises a cross connector adapted to receive injections from opposing sides of the external blood loop.

In some embodiments of the apparatus, the assembly means further comprises an alignment means adapted to guide insertion of the sensor into a venous flow device. For example, the alignment means can comprise a needle having a lumen, or other piercing device. The piercing device can be fixed or removable, and optionally, includes a slot or other means to allow removal of the piercing device without removing the sensor. The sensor shape can also be modified to facilitate removal of the piercing device without disturbing the sensor position.

In a typical embodiment, the assembly means comprises a lure lock connector, of either the fixed or rotating variety. Variations on a lure lock, or a custom cap or housing can serve as an assembly means, providing a means for introducing the sensor into the area of blood flow while protecting the integrity of the venous flow. The assembly means can be designed to clip into place for secure and accurate positioning. A clip can be used to attach and/or release the apparatus to/from the venous flow device.

The apparatus can further comprise a medication delivery system, wherein the medication delivery system comprises means for infusing a medication into the venous flow device. In addition, the apparatus can include a feedback loop, wherein an output from the sensor is communicated to the medication delivery system. In such a closed loop system, sensor output can control infusion of medication, such as insulin and/or glucose, or other desired medication whose dosage would be adjusted on the basis of sensor-gathered information.

The sensor can be any biocompatible sensor, suitable for short or long-term use. In preferred embodiments, the sensor is an optical, optochemical, molecular recognition, enzymatic or electrochemical sensor. One example of a sensor includes a glucose sensor.

In some embodiments, the sensor is operatively coupled to a monitor or other device. The coupling can be direct or telemetric, and facilitates continuous or regular monitoring of the subject's analyte levels. For example, in a hospital setting, the apparatus can be used to monitor a patient's glucose or other analyte level from a remote location, such as a nursing station.

The invention additionally provides a method of introducing a sensor into the circulating blood of a subject. The method comprises contacting a venous flow device with the circulating blood of the subject and introducing an apparatus of the invention into the venous flow device. The sensor contacts the circulating blood of the subject as the blood flows through the venous flow device. In one embodiment, the venous flow device comprises an external blood loop having a port adapted to receive the apparatus. Optionally, the external blood loop further comprises a second port adapted to receive an alignment means. The method can further comprise introducing an alignment means into the external blood loop from a side opposing the port adapted to receive the apparatus prior to introducing the apparatus.

In one embodiment, the method further comprises introducing an alignment means into the port prior to or simultaneously with introduction of the apparatus. The alignment means can be removed following introduction of the apparatus. Alternatively, the venous flow device can be a catheter.

BRIEF DESCRIPTION OF THE DRAWINGS

FIG. 1A illustrates an external blood loop 10 containing a T-connector 12 and an apparatus 14 of the invention wherein the sensor 16 protrudes into the blood loop 10 upon connection of the assembly means 14 to the T-connector 12 via a lure lock 18.

FIG. 1B shows how the sensor 16 extends from the sensor end 20 of the assembly means 14 and how the assembly means 14 is adapted for coupling with the T-connector 12 of the blood loop 10.

FIG. 2 illustrates an alternative embodiment of the assembly means 14 that incorporates a T-connector 12 and has been plumbed into the external blood circuit 10. In this configuration, the sensor (not visible in this view) orientation is perpendicular to the blood flow through the circuit 10.

FIG. 4A illustrates a cross-connector 40 capable of insertion in an external blood circuit. The cross-connector 40 provides two injection sites 42, 44 opposing one another. A piercing device 46 is introduced through the first injection site 44 and exits from the second injection site 42, providing a guide for insertion of the sensor 16 through the second injection site 42. The assembly means 14 includes guides 48 to facilitate alignment of the sensor 16 during insertion.

FIG. 4B shows the embodiment of FIG. 4A after the piercing device 46 has passed through both injection sites 42, 44, exposing a guide 46 for sensor 16 insertion.

FIG. 4C shows the embodiment of FIGS. 4A and 4B after the sensor 16 has been positioned in the cross connector of the blood circuit 40 and the piercing device 46 removed.

FIG. 5A illustrates an introducer catheter 50 used to introduce the sensor 16 into the circuit 10 via a T-connector 12.

FIG. 5B shows the embodiment of FIG. 5A after the introducer catheter 50 has been inserted and the sensor 16 is being introduced into the circuit 10.

FIG. 5C shows the sensor 16 in position, with its distal tip 52 positioned perpendicular to the flow of blood through the connector 12.

FIGS. 10A-10C illustrate various embodiments of an assembly means 14 that includes a side port 92 and is coupled to an intravenous catheter 90.

In FIG. 12A, the support 300 is a catheter and the conductive material 302 protrudes from the lumen 304 of the catheter. In FIG. 12B, the conductive material 302 is affixed to the external surface 310 of the catheter 300 and protrudes beyond the distal end 306 of the catheter 300. In FIG. 12C, the functions of the support 300 and substrate 308 are conflated, such that only the conductive material 302 and the substrate (e.g., a 0.005-0.007 inch thick polyimide tape) 308 are necessary. In this latter embodiment, the conductive material 302 protrudes laterally with respect to the distal end 306.

DETAILED DESCRIPTION

Figure 3A:
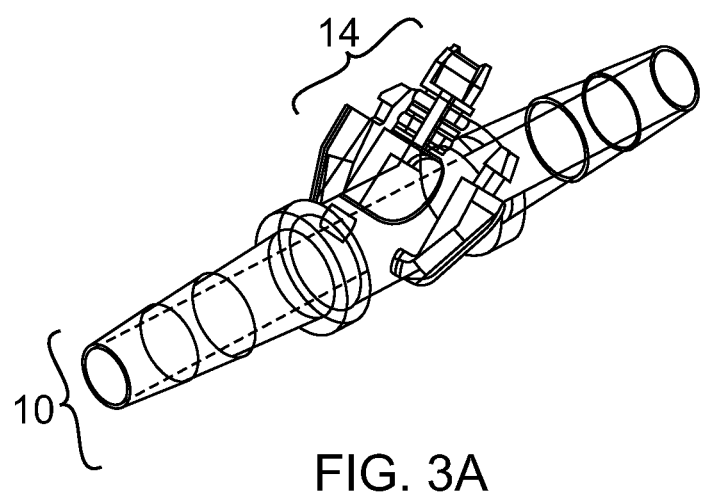
FIG. 3A illustrates a variation on the embodiment shown in FIG. 2, wherein the sensor (not visible in this view) enters the circuit 10 at an angle, with an orientation that is more parallel to the flow of blood. A portion of the assembly means 14 is excluded from this view to more clearly illustrate the entrance of the sensor into the blood circuit.
Figure 3B:
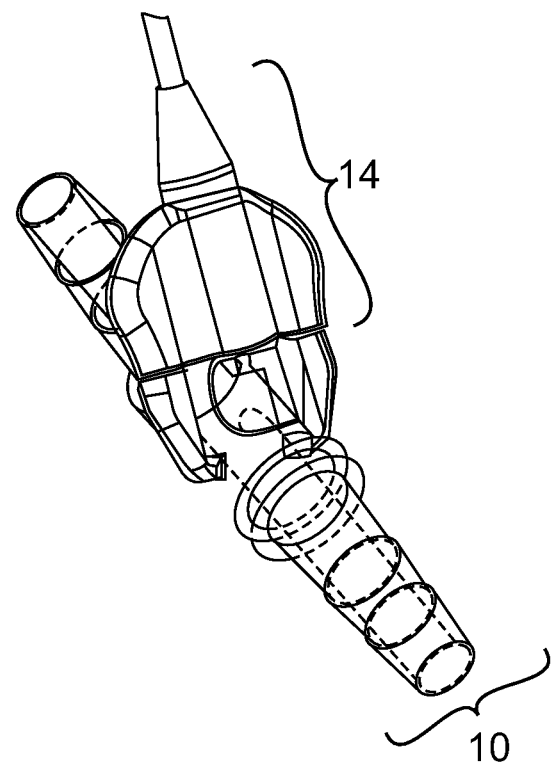
FIG. 3B completes the illustration of FIG. 3A by including the remainder of the assembly means 14.
Figure 6B:
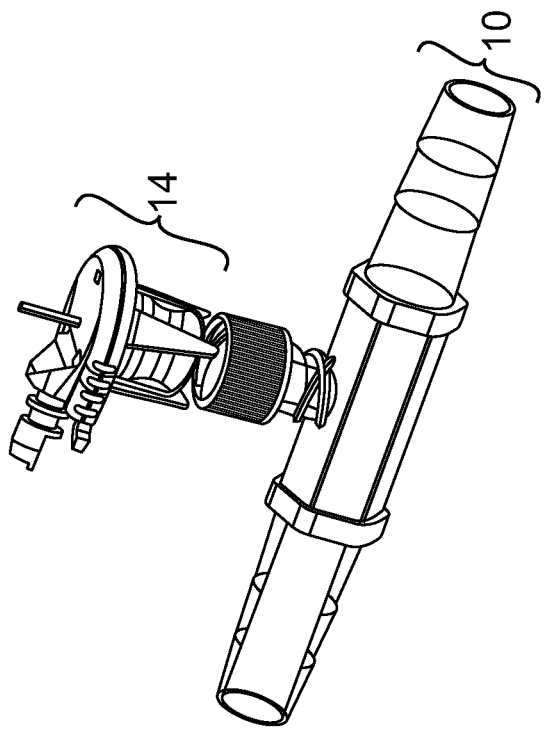
FIG. 6B shows the assembly means 14 of FIG. 6A after it has been inserted into the venous flow device 10.
Figure 6A:
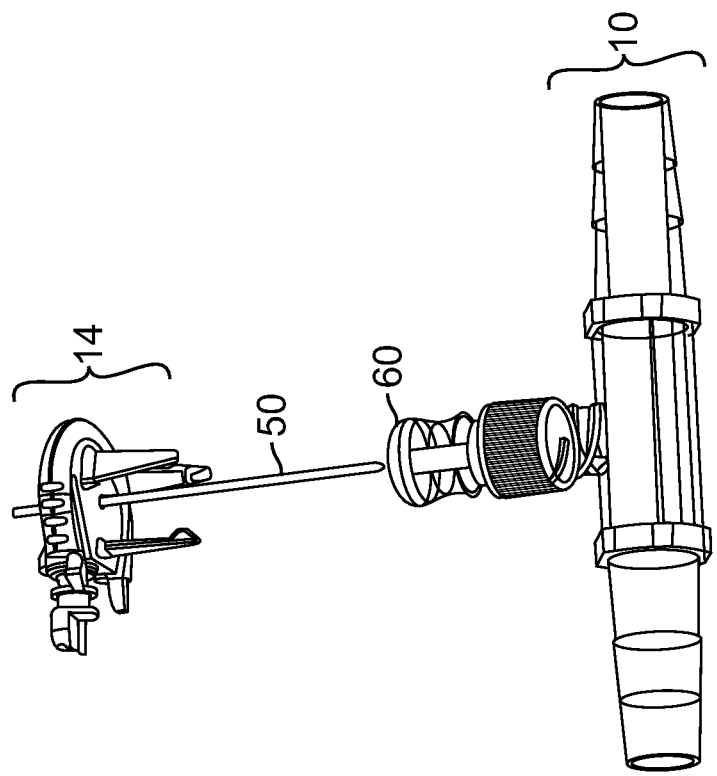
FIG. 6A illustrates an assembly means 14 that includes a piercing device 50 for introducing the sensor (not visible in this view) into a venous flow device 10, e.g., via a septum 60.
Figure 7A:
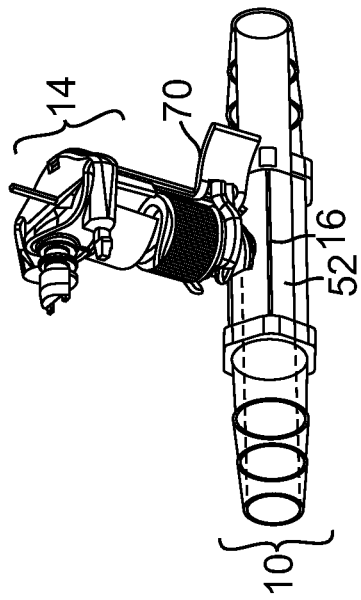
FIG. 7A illustrates an assembly means 14 that includes, in addition to a piercing device 50, a clip 70 that can be activated for attachment to or release from the venous flow device (not visible in this view), and which further guides accurate placement of the sensor (not visible in this view).
Figure 7C:
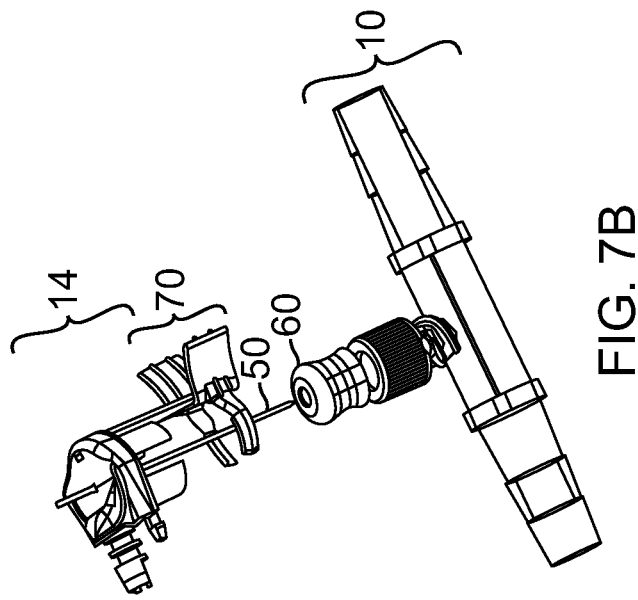
FIG. 7C shows the sensor 50 in position, with its distal tip 52 positioned perpendicular to the flow of blood through the venous flow device 10.
Figure 7B:
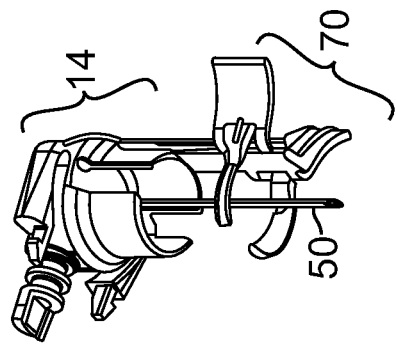
FIG. 7B shows the embodiment of FIG. 7A as it is being introduced into the circuit 10.
Figure 8D:
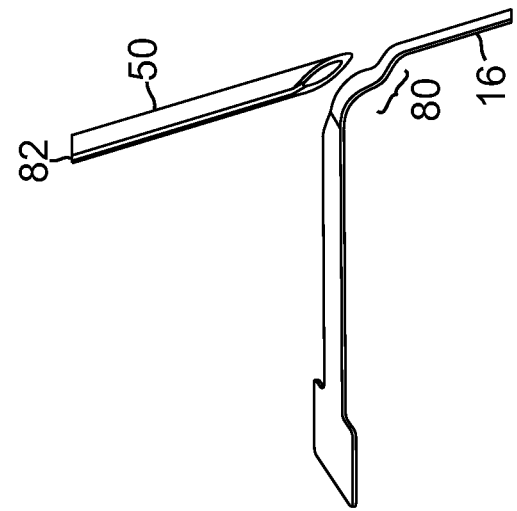
FIG. 8D shows the sensor 16 and piercing device 50 of FIG. 8C, with the piercing device 50 separated from the sensor 16.
Figure 8C:
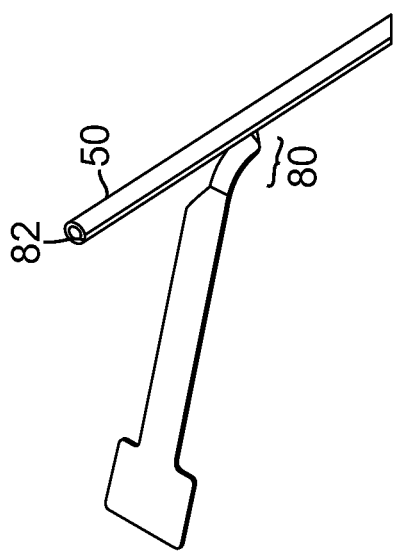
FIG. 8C shows the sensor 16 of FIG. 8B inside the slot 82 of the piercing device 50 shown in FIG. 8A.
Figure 8B:
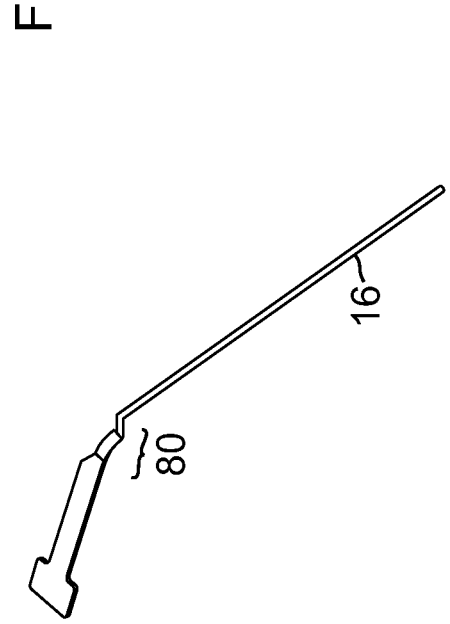
FIG. 8B shows a sensor 16 for use with the piercing device 50 of FIG. 8A, which sensor 16 has a jog 80 along its length to permit removal of the piercing device 50 while leaving the sensor 16 in place.
Figure 8A:
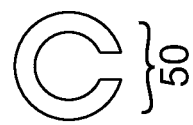
FIG. 8A illustrates a cross-sectional view of a needle 50, or piercing device 50, modified to include a slot 82 to facilitate removal after introduction of the sensor (not visible in this view).
Figure 9C:
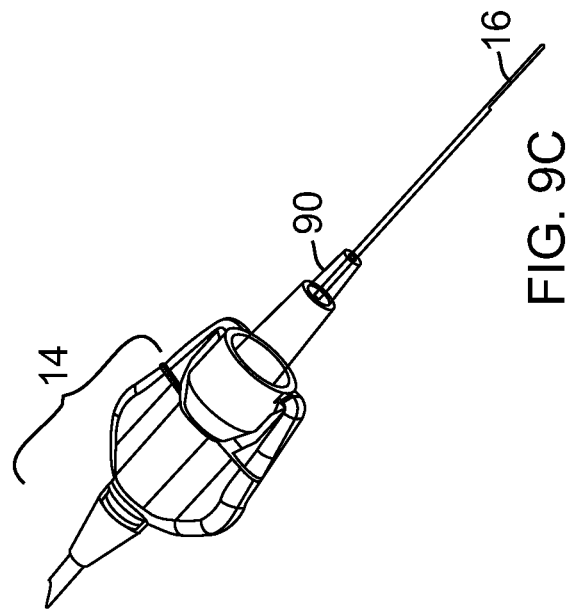
FIG. 9C shows a variation on the embodiment of FIG. 9B.
Figure 9B:
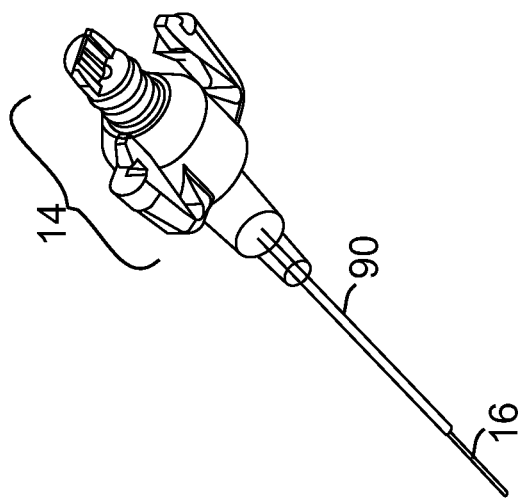
FIG. 9B shows the embodiment of FIG. 9A after insertion of the sensor 16 into the catheter 90.
Figure 9A:
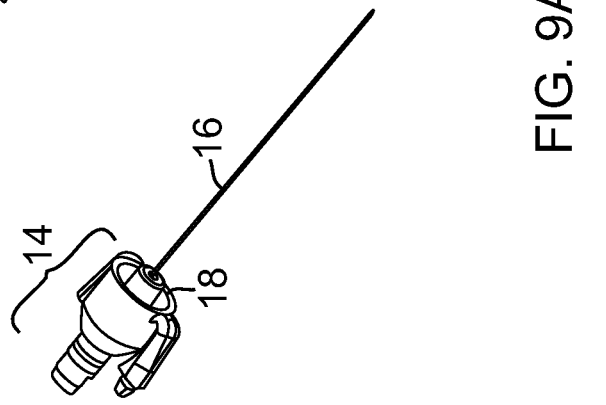
FIG. 9A illustrates an assembly means 14 adapted for coupling to an intravenous catheter 90 via a lure lock 18.

All scientific and technical terms used in this application have meanings commonly used in the art unless otherwise specified. As used in this application, the following words or phrases have the meanings specified.

As used herein, the "sensor end" of the assembly means refers to the portion of surface of the assembly means that is enclosed when the assembly means is coupled to a venous flow device. The sensor is affixed to the sensor end of the assembly means and is positioned within the venous flow device upon coupling of the assembly means to a venous flow device.

As used herein, the "exterior face" of the assembly means refers to the portion of surface of the assembly means that remains exposed when the assembly means is coupled to a venous flow device.

As used herein, "affixed to" means attached to, stuck to, against or fused with such that a substance affixed to an object remains substantially attached to or closely associated with the object. In one example of a substrate affixed to a conductive material, the substrate and conductive material are fabricated as a single element, which can then be positioned on a support.

As used herein, "hydrophilic material" means a material having a strong tendency to bind or absorb water, which is sufficient to result in swelling and formation of gels. This property is characteristic of some natural polymers, including carbohydrates, proteins and man-made polymers (e.g., hydrogels).

As used herein, "a" or "an" means at least one, and unless clearly indicated otherwise, includes a plurality.

Overview

The invention provides methods and apparatus for detecting an analyte in tissue, typically blood. The apparatus is particularly suited for uses that involve bringing a sensor into direct contact with blood in vivo or in an extracorporeal circuit. The apparatus comprises a sensor that detects the presence of an analyte and, optionally, a support and/or an assembly means. The sensor comprises an elongated conductive material having a protrudent end, the protrudent end comprising an electrode that detects the presence of an analyte; a substrate affixed to the conductive material; and, in some embodiments, a support having an external surface, a proximal end, and a distal end. The conductive material is positioned on the support and the protrudent end of the conductive material protrudes beyond the distal end of the support.

The assembly means has a sensor end, wherein the sensor end of the assembly means is affixed to the sensor, and the assembly means is adapted for coupling with a venous flow device. By coupling with a venous flow device, the assembly means brings the sensor into direct contact with blood flowing through the venous flow device. Examples of venous flow devices that bring the sensor into direct contact with the blood of a subject include, but are not limited to, intravenous catheters and external blood loops, such as are used in extra corporeal membrane oxygenation or hemodialysis.

Sensor

The sensor can be any biocompatible sensor, suitable for short or long-term use. In preferred embodiments, the sensor is an optical, optochemical, molecular recognition, enzymatic or electrochemical sensor. One example of a sensor includes a glucose sensor. The sensor may also measure, in addition to, or in lieu of blood glucose concentration, the concentration of oxygen, potassium, hydrogen potential (pH), lactate, one or more minerals, analytes, chemicals, proteins, molecules, vitamins, and the like, and/or other physical characteristics such as temperature, pulse rate, respiratory rate, pressure, and the like.

An exemplary sensor includes a working electrode plated with an enzyme. A sensor can have a reference electrode, a working electrode, and a counter electrode deposited on a polymeric sheet or other substrate. The sensor further includes a series of bonding pads. The entire electrode array can then be coated with a layer of a polymer. The electrodes can be made of any conductive surface, e.g., gold, platinum, palladium, chromium, copper, aluminum, pyrolitic carbon, composite material (e.g., metal-polymer blend), nickel, zinc, titanium, or an alloy, such as cobalt-nickel-chromium, or titanium-aluminum-vanadium, which is deposited on any of a variety of suitable materials, including glass, polyimide or polyester. In some embodiments, the electrode array includes a flex-circuit layout/design. Of course, those skilled in the art will recognize that variations of the above components, and other types of electrodes can be used in the invention. The sensor can be coated further with a hydrophilic polymer, which provides for reduction of biofouling and enhanced sensor performance in a biological environment.

Figure 12A:
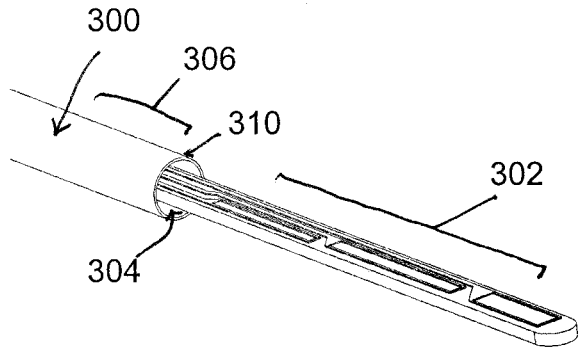
FIGS. 12A-C illustrate 3 embodiments of the apparatus.
Figure 12B:
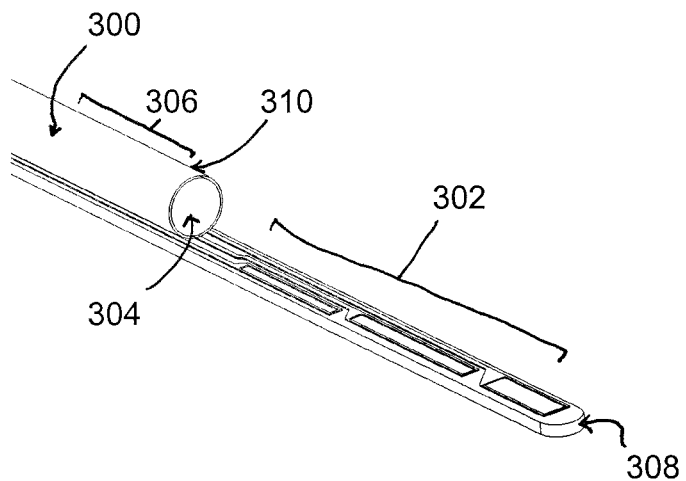
Figure 12C:
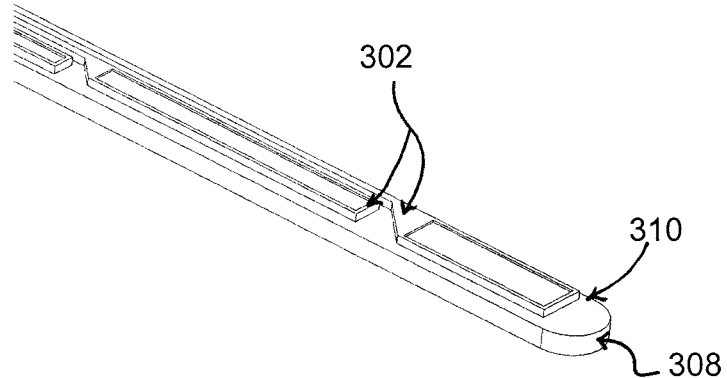

The sensor comprises an elongated conductive material having a protrudent end, the protrudent end comprising an electrode that detects the presence of an analyte; a substrate affixed to the conductive material; and a support having an external surface, a proximal end, and a distal end. The conductive material is positioned on the support and the protrudent end of the conductive material protrudes beyond the distal end of the support. In a typical embodiment, the protrudent end protrudes longitudinally beyond the distal end (e.g., as shown in FIG. 12A-12B). Alternatively, such an embodiment in which the substrate and support functions are conflated, the protrudent end may protrude laterally from the distal end (e.g., as shown in FIG. 12C). The substrate optionally comprises an insulative layer that covers the conductive material and does not cover the most distal portion where the electrode makes contact with and detects the analyte.

In a typical embodiment, the sensor comprises a thin film vascular sensor such as described in U.S. Pat. Nos. 5,497,772, 5,660,163, 5,750,926, 5,791,344, 5,917,346, 5,999,848, 5,999,849, 6,043,437, 6,081,736, 6,088,608, 6,119,028, 6,259,937, 6,472,122, and 6,671,554, and U.S. patent application Ser. Nos. 10/034,627 (published as U.S. patent publication no. 2003/0078560 A1, Apr. 24, 2003), Ser. No. 10/331,186 (published as U.S. patent publication no. 2004/0061232 A1, Apr. 1, 2004), Ser. No. 10/671,996 (published as U.S. patent publication no. 2004/0061234 A1, Apr. 1, 2004), Ser. No. 10/335,574 (published as U.S. patent publication no. 2004/0064156 A1, Apr. 1, 2004), Ser. No. 10/334,686 (published as U.S. patent publication no. 2004/0064133 A1, Apr. 1, 2004), and Ser. No. 10/365,279 (published as U.S. patent publication no. 2003/0220552 A1, Nov. 27, 2003), which are herein incorporated by reference.

In some embodiments, the biosensor is an optical affinity sensor, e.g., having a glucose binding site. The sensor, which includes a reflective substrate, can be coated with a hydrophilic, biocompatible and glucose permeable coating. Optical sensors for detection of analytes are described in U.S. Pat. Nos. 6,256,522, and 5,143,066.

Other examples of sensors are described in U.S. Pat. Nos. 4,671,288 (electrochemical sensor); U.S. Pat. No. 5,320,725 (amperometric sensor); U.S. Pat. No. 5,403,700 (polyimide-based sensor design); and U.S. Pat. No. 5,540,828 (sensor with a polymer-modified surface). Those skilled in the art can readily appreciate the ability to adapt the teachings of the present invention to a variety of known sensor types and configurations.

A preferred sensor for use with the invention comprises a thin film, such as a Kapton® sheet (DuPont), affixed to a rigid substrate, such as glass. A fabrication method for producing thin film electrochemical sensors is described in U.S. Pat. No. 5,391,250. By this method, one or more sensors are formed on a rigid flat substrate, such as a glass plate. The sensors are formed in a manner compatible with photolithographic mask and etch techniques, but wherein the sensors are not physically adhered or attached directly to the substrate. Accordingly, finished sensors can be removed quickly and easily from the substrate by simple lift-off separation.

In one embodiment, a thick film is used. For example, rather than a 0.001 inch thin film, the film is several-fold thicker, typically about 0.005 to about 0.007 inch. In this embodiment, the substrate comprises a polyimide film that is about 0.005 to about 0.007 inch in thickness. In this latter embodiment, the substrate serves as the support due to the substantial support provided by the polyimide film (FIG. 12C). A separate element for support is not necessary, although could be added if desired, such as a catheter for delivery of other substance(s) to the site. As with the thin film, the thick film can comprise a conventional material, such as a Kapton® sheet (DuPont). Those of skill in the art understand that a range of thicknesses are possible for the substrate comprising a polyimide film. In certain embodiments of the invention, the film is about 0.1, to about 0.125, 0.15, 0.175 or 0.2 millimeters in thickness.

The conductive material can be surrounded or encompassed by the support or be positioned on the support. In addition to adding rigidity and strength to the sensor, the support can create an improved seal, for example, upon insertion into a septum. Positioning the conductive material inside the lumen of a cylindrical or tubular support, as shown in FIG. 12A, can improve the sealing. The exterior surface of the tube provides a nice, smooth, round surface to seal against. The interior, e.g., around the conductive material, can be sealed with silicone or UV curable sealant. In other embodiments, such as shown in FIG. 12B-12C, the conductive material is positioned on the external surface of the support. Those skilled in the art will appreciate variations on the shape and configuration of the support that can be tailored to particular objectives.

Each sensor comprises a plurality of elongated thin film conductors formed between an underlying insulative thin film base layer and an overlying insulative thin film cover layer. Apertures are formed in the cover layer to expose distal end electrodes and proximal end contact pads. In a glucose monitoring application, the thin film sensor is placed so that the distal end electrodes are in direct contact with patient blood, and wherein contact pads are disposed externally for convenient connection to a monitoring device.

The substrate comprises a rigid and flat structure suitable for use in photolithographic mask and etch processes. In this regard, the substrate defines an upper surface having a high degree of uniform flatness. A polished glass plate may be used defining the smooth upper surface. Alternative substrate materials include, for example, stainless steel, aluminum, and plastic materials such as Delrin, etc. In some embodiments, complete rigidity of the substrate is not desired, as some flexibility may be desired for insertion into a blood vessel, particularly for sensors of extended length (e.g., for use with a 22 gauge intravenous infusion catheter). In such an embodiment, sufficient rigidity is provided at the distal end to facilitate electrode manufacture, but the bulk of the sensor length is sufficiently flexible to permit threading of the sensor through venous flow devices or blood vessels.

A thin layer film of a curable adhesive, provided as shown in the form of a die-cut strip or frame, is applied in a closed loop pattern to the perimeter of the substrate. The base layer is then placed on the substrate, with a perimeter of the base layer in intimate seated contact upon the adhesive strip. The thus-assembled components define a shallow cavity between a central portion of the base layer and the underlying substrate, with the adhesive strip circumscribing the peripheral edge of the cavity. In one embodiment, the base layer comprises a thin film sheet of insulative material, such as polyimide having a film thickness on the order of about 0.003 inch. The adhesive strip comprises an epoxy resin, which may be impregnated with fiberglass, such as an epoxy resin available from 3M Aerospace Division of Springfield, Mo., under the name AF-163-205T. Alternative adhesive materials may include ultraviolet curable adhesives, etc. Moreover, if desired for improved adhesion between the base layer and the adhesive strip, a perimeter region of the base layer may be surface etched.

In one embodiment, the sensor further comprises a coating. The sensor can be coated with a medicinal agent, such as an anticoagulant, or an antimicrobial agent. In one embodiment, the coating contains a hydrophilic polymer. Examples of hydrophilic polymers include, but are not limited to, polyhydroxyethylmethacrylate (PHEMA), polysaccharide, polyacrylamide, polyurea, polyethylene oxide (PEO) containing polyurethane, PEO containing polyurea and cross-linked PEO. Optionally, the coating comprises a stiffening agent.

Sensors of the invention can also be incorporated into a wide variety of medical systems known in the art. Sensors of the invention can be used for example in a closed loop infusion systems designed to control the rate that medication is infused into the body of a user. Such a closed loop infusion system can include a sensor and an associated meter, which generates an input to a controller, which in turn operates a delivery system (e.g. one that calculates a dose to be delivered by a medication infusion pump). In such contexts, the meter associated with the sensor may also transmit commands to, and be used to remotely control, the delivery system. Illustrative systems are disclosed for example in U.S. Pat. Nos. 6,558,351 and 6,551,276; PCT Application Nos. US99/21703 and US99/22993; as well as WO 2004/008956 and WO 2004/009161, all of which are incorporated herein by reference.

In general, the analyte sensor apparatus structure comprises a base layer (substrate) and a conductive layer disposed upon the base layer that includes one or more electrodes. For example, the conductive layer can include a working electrode, a reference electrode and/or a counter electrode. These electrodes can be spaced in proximity, or alternatively are spaced distally according to the preferred design. The sensor apparatus design is such that certain electrodes (e.g. the working electrode) can be exposed to the blood, containing the analyte to be sensed in the sensor apparatus. The sensor apparatus design is such that certain electrodes (e.g. the reference electrode) are not exposed to the blood to be analyzed.

Typically, the analyte sensor apparatus includes an analyte sensing layer disposed on the conductive layer, typically covering a portion or all of the working electrode. This analyte sensing layer detectably alters the electrical current at the working electrode in the conductive layer in the presence of an analyte to be sensed. As disclosed herein, this analyte sensing layer typically includes an enzyme or antibody molecule or the like that reacts with the analyte of interest in a manner that changes the concentrations of a molecule that can modulate the current at the working electrode. Illustrative analyte sensing layers comprise an enzyme such as glucose oxidase (e.g. for use in glucose sensors) or lactate oxidase (e.g. for use in lactate sensors). Typically, the analyte sensing layer further comprises a carrier protein in a substantially fixed ratio with the analyte sensing compound (e.g. the enzyme) and the analyte sensing compound and the carrier protein are distributed in a substantially uniform manner throughout the analyte sensing layer.

Optionally, the analyte sensing layer has a protein layer disposed thereon and which is typically between the analyte sensing layer and an analyte modulating layer. A protein within the protein layer can be an albumin such as bovine serum albumin or human serum albumin. Typically this protein is cross-linked. Without being bound by a specific scientific theory, it is believed that this separate protein layer enhances sensor function and provides surprising functional benefits by acting as a capacitor that diminishes sensor noise (e.g. spurious background signals). For example, in the sensors of the invention, some amount of moisture may form under the analyte modulating membrane layer of the sensor, the layer which regulates the amount of analyte that can contact the enzyme of the analyte sensing layer. This moisture may create a compressible layer that shifts within the sensor as a patient using the sensor moves. Such shifting of layers within the sensor may alter the way that an analyte such as glucose moves through the analyte sensing layers in a manner that is independent of actual physiological analyte concentrations, thereby generating noise. In this context, the protein layer may act as a capacitor by protecting an enzyme from contacting the moisture layer. This protein layer may confer a number of additional advantages such as promoting the adhesion between the analyte sensing layer and the analyte modulating membrane layer. Alternatively, the presence of this layer may result in a greater diffusion path for molecules such as hydrogen peroxide, thereby localizing it to the electrode sensing element and contributing to an enhanced sensor sensitivity.

Typically, the analyte sensing layer and/or the protein layer disposed on the analyte sensing layer has an adhesion promoting layer disposed thereon. Such adhesion promoting layers promote the adhesion between the analyte sensing layer and a proximal layer, typically an analyte modulating layer.

This adhesion promoting layer preferably comprises a silane compound such as γ-aminopropyltrimethoxysilane which is selected for its ability to promote optimized adhesion between the various sensor layers and functions to stabilize the sensor. Interestingly, sensors having such a silane containing adhesion promoting layer exhibit unexpected properties, including an enhanced overall stability. In addition, silane containing adhesion promoting layers provide a number of advantageous characteristics in addition to an ability to enhancing sensor stability and can for example play a beneficial role in interference rejection as well as in controlling the mass transfer of one or more desired analytes.

In some embodiments of the invention, the adhesion promoting layer further comprises one or more compounds that can also be present in an adjacent layer, such as the polydimethyl siloxane (PDMS) compounds, that limit the diffusion of analytes such as glucose through the analyte modulating layer. The addition of PDMS to the adhesion promoting layer, for example, can be advantageous in contexts where it diminishes the possibility of holes or gaps occurring in the AP layer as the sensor is manufactured.

Typically the adhesion promoting layer has an analyte modulating layer disposed thereon which modulates the diffusion of analytes therethrough. The analyte modulating layer can include compositions (e.g. polymers and the like) that enhance the diffusion of analytes (e.g. oxygen) through the sensor layers and consequently enrich analyte concentrations in the analyte sensing layer and/or compositions that limit the diffusion of analytes (e.g. glucose) through the sensor layers and consequently limit analyte concentrations in the analyte sensing layer. An illustrative example of this is a hydrophilic glucose limiting membrane (i.e. that limits the diffusion of glucose therethrough) comprising a polymer such as polydimethyl siloxane or the like.

Typically the analyte modulating layer further comprises one or more cover layers, which are typically electrically insulating protective layers, disposed on at least a portion of the sensor apparatus (e.g. covering the analyte modulating layer). Acceptable polymer coatings for use as the insulating protective cover layer can include, but are not limited to, non-toxic biocompatible polymers such as silicone compounds, polyimides, biocompatible solder masks, epoxy acrylate copolymers, or the like. A preferred cover layer comprises spun on silicone. Typically the cover layer further includes an aperture that exposes at least a portion of a sensor layer (e.g. analyte modulating layer) to a solution comprising the analyte to be sensed.

The analyte sensors described herein can be polarized cathodically to detect, for example, changes in current at the working cathode that result from the changes in oxygen concentration proximal to the working cathode that occur as glucose interacts with glucose oxidase. Alternatively, the analyte sensors described herein can be polarized anodically to detect for example, changes in current at the working anode that result from the changes in hydrogen peroxide concentration proximal to the working anode that occur as glucose interacts with glucose oxidase. In typical embodiments of the invention, the current at the working electrode(s) are compared to the current at a reference electrode(s) (a control), with the differences between these measurements providing a value that can then be correlated to the concentration of the analyte being measured. Analyte sensor designs that obtain a current value by obtaining a measurement from a comparison of the currents at these dual electrodes are commonly termed, for example, dual oxygen sensors.

In some embodiments of the invention, the analyte sensor apparatus is designed to function via anodic polarization such that the alteration in current is detected at the anodic working electrode in the conductive layer of the analyte sensor apparatus. Structural design features that can be associated with anodic polarization include a sensor configuration comprising a working electrode that is an anode, a counter electrode that is a cathode and a reference electrode. The appropriate analyte sensing layer is then selectively disposed on the appropriate portion of the surface of the anode within this design configuration. Optionally, this anodic polarization structural design includes anodes, cathodes and/or working electrodes having different sized surface areas. For example, this structural design includes features where the working electrode (anode) and/or the coated surface of the working electrode is larger than the counter electrode (cathode) and/or the coated surface of the counter electrode. In this context, the alteration in current that can be detected at the anodic working electrode is then correlated with the concentration of the analyte.

In certain illustrative examples of this embodiment of the invention, the working electrode is measuring and utilizing hydrogen peroxide in the oxidation reaction, wherein hydrogen peroxide is produced by an enzyme such as glucose oxidase or lactate oxidase upon reaction with glucose or lactate, respectively. Such embodiments of the invention relating to electrochemical glucose and/or lactate sensors having such hydrogen peroxide recycling capabilities are desirable because the recycling of this molecule reduces the amount of hydrogen peroxide that can escape from the sensor into the environment in which it is placed. In this context, implantable sensors that are designed to reduce the release of tissue irritants such as hydrogen peroxide will have improved biocompatibility profiles. Optionally, the analyte modulating layer (e.g. a glucose limiting layer) can include compositions that inhibit the diffusion of hydrogen peroxide out into the environment in which the sensor is placed. Consequently, such embodiments of the invention improve the biocompatibility of sensors that incorporate enzymes that produce hydrogen peroxide by incorporating hydrogen peroxide recycling elements disclosed herein.

Certain embodiments of the analyte sensors of the invention that comprise a base layer, a conductive layer, an analyte sensing layer, an optional protein layer, an adhesion promoting layer, and analyte modulating layer and a cover layer exhibit a number of advantageous properties. For example, in sensors that are structured to function via anodic polarization versus those structured to function via cathodic polarization, differences in the electrochemical reactions in the analyte sensing layer as well as at the electrode surface generate and/or consume different chemical entities, thereby altering the chemical environment in which the various sensor elements function in different polarities. In this context, the sensor structure disclosed herein provides a surprisingly versatile device that is shown to function with an unexpected degree of stability under a variety of different chemical and/or electrochemical conditions.

In certain embodiments of the invention disclosed herein (e.g., those having hydrogen peroxide recycling capabilities) the sensor layer has a plurality of electrodes including a working electrode (e.g. an anode) and a counter electrode (e.g. a cathode), both of which are coated with a analyte sensing layer comprising an enzyme such as glucose oxidase or lactate oxidase. Such sensor designs have an enhanced sensitivity. Without being bound by a specific theory, these properties may result from the enhanced oxidation of hydrogen peroxide at the surface of a working or a counter electrode, which produces additional oxygen that can be utilized in the glucose sensing reaction. Therefore this recycling effect may reduce the oxygen dependent limitations of certain sensor embodiments disclosed herein. Moreover, this design may result in a sensor having a working electrode that can readily reduce available hydrogen peroxide and consequently has a lower electrode potential. Sensors designed to function with lower electrode potentials are preferred because high electrode potentials in sensors of this type can result in a gas producing hydrolysis reaction, which can destabilize the sensors (due to the disruption of sensor layers from gas bubbles produced by hydrolysis reactions). In addition, in sensor embodiments wherein the counter electrode is coated with a very thin layer of an analyte sensing layer comprising an enzyme such as glucose oxidase or lactate oxidase, the hydrogen peroxide generated in the enzymatic reaction is very close to the reactive surface of the counter electrode. This can increase the overall efficiency of the sensor in a manner that allows for the production of compact sensor designs which include for example, counter electrodes with smaller reactive surfaces.

A specific illustrative example of an analyte sensor apparatus for implantation within a mammal is a peroxide sensor having a first, base layer, typically made from a ceramic such as alumina. A subsequent layer disposed upon the base layer is conductive layer having a plurality of electrodes, including an anodic working electrode and a reference electrode. A subsequent layer disposed on the conductive layer is an analyte sensing layer that includes crosslinked glucose oxidase, which senses glucose and consequently generates hydrogen peroxide. In the presence of this hydrogen peroxide, the anodic working electrode experiences a measurable increase in current as the hydrogen peroxide generated contacts this anode in the conductive layer and is oxidized. The reference electrode serves as a control and is physically isolated from the working electrode and the hydrogen peroxide generated. This analyte sensing layer is preferably less than 1, 0.5, 0.25 or 0.1 microns in thickness and comprises a mixture of crosslinked human serum albumin in a substantially fixed ratio with the crosslinked glucose oxidase, with the glucose oxidase and the human serum albumin being distributed in a substantially uniform manner throughout the sensor layer. A subsequent layer disposed on the sensor layer is a protein layer comprising crosslinked human serum albumin. A subsequent layer disposed on the protein layer is an adhesion promoting layer, which promotes the adhesion between the analyte sensing layer and/or the protein layer and an analyte modulating layer disposed upon these layers. This adhesion promoting layer comprises a silane composition. A subsequent layer disposed on the adhesion promoting layer is the analyte modulating layer in the form of a hydrophilic glucose limiting membrane comprising PDMS. A subsequent layer is a cover layer, typically composed of silicone, which is disposed on at least a portion of the analyte modulating layer, wherein the cover layer further includes an aperture that exposes at least a portion of the analyte modulating layer to the external glucose containing environment so that the glucose can access the analyte sensing layer on the working electrode.

This peroxide sensor apparatus functions via anodic polarization such that the hydrogen peroxide signal that is generated by glucose diffusing through the analyte modulating layer and then reacts with the glucose oxidase in the analyte sensing layer creates a detectable change in the current at the anodic working electrode in the conductive layer of the sensor that can be measured by an amperometer. This change in the current at the anodic working electrode can then be correlated with the concentration of glucose in the external environment. Consequently, a sensor of this design can act as a peroxide based glucose sensor.

Hydrophilic Coating

In some embodiments, the sensor includes a hydrophilic coating. The coating applied to a sensor embodiment of the invention includes a hydrophilic polymer. Examples of hydrophilic materials include, but are not limited to, polyureas, polyamides, polyurethanes, acrylates, polyesters, polyethylene oxide (PEO) or cross-linked PEO. A preferred hydrophilic material for use in accordance with the invention is a PEO containing polyurethane or PEO containing polyurea. PEOs can be cross-linked by a variety of methods known in the art, including via the use of a gas plasma, or ionizing radiation such as electron or gamma sources, for example.

It is desirable to obtain a very hydrophilic membrane at the interface between the sensor and the biological environment. Accordingly, the coating is at least sufficiently hydrophilic to achieve swelling and gel formation. Preferably, the coating is sufficiently hydrophilic that, upon contact with a wet environment, it achieves a swell volume of at least about two, three, four or five times the thickness of the coating in a dry environment. Preferably, the coating is sufficiently hydrophilic, oxygen permeable and/or optically transparent so as to not change the overall analyte sensing capability of the sensor. Ideally, the coating achieves the maximal swell volume that does not disrupt adhesion with the underlying material.

Preferred hydrophilic materials include, but are not limited to, PEO containing polyurethanes, such as HydroMed™ TPH-D640 (available from CardioTech International). Such a polyurethane is suitable for application over the top of polymeric coatings currently in use with glucose sensors, such as glucose limiting polymer (GLP; MiniMed, Inc., Northridge, Calif.). In such applications, the hydrophilic material preferably does not limit glucose and is readily incorporated into the sensor production process.

The hydrophilic material is applied by conventional means, including dip-coating or spraying the coating onto the sensor surface, e.g., over the GLP or optochemical sensing polymer. Typically, dip-coating is used to coat only the distal end of the sensor. The preferred polymer does not impede the diffusion of glucose, is soluble in a volatile organic solvent, such as tetrahydrofuran (THF) or isopropyl alcohol or mixture thereof (e.g., 25/75), that is suitable for spraying without disrupting the original surface. Damage to the underlying surface could affect the mass transfer properties of the underlying material and result in erratic sensor behavior. Alternatively, the hydrophilic material can be applied by painting or other means known in the art.

Therapeutic Agents

A medicinal or therapeutic agent can be incorporated into the hydrophilic material for the coating of the sensor. The agent is selected in accordance with the desired effect. For example, the objective may be to prevent or minimize inflammation or microbial infection. Examples of therapeutic agents include, but are not limited to, anti-inflammatory, anti-bacterial, anti-viral, anti-coagulant, and disinfecting agents, such as dexamethasone, cefazolin, and benzalkonium chloride, and/or a growth factor. In some embodiments, the therapeutic agent may be an anti-proliferative agent that kills growing cells such as microbial organisms or reactive cells. In a preferred embodiment, the hydrophilic coating includes an anti-inflammatory agent, such as dexamethasone or a salt thereof. Suitable water-soluble salts of dexamethasone include, but are not limited to, the sodium phosphate or acetate salts. Dexamethasone serves to reduce inflammation and also to deactivate macrophages, which allows for enhanced sensor performance.

Polymer Layer

In a preferred embodiment, the polymer layer comprises polyurea (see, e.g., U.S. Pat. Nos. 5,777,060 and 5,786,439). Examples of a suitable polymer layer for a biosensor include, but are not limited to, glucose limiting polymer (GLP; Medtronic MiniMed, Inc., Northridge, Calif.). Other formulations of the polymer layer can be selected in accordance with the desired use. For example, U.S. Pat. Nos. 5,777,060 and 5,786,439 describe coatings suitable for use with biosensors, particularly for use with glucose oxidase and glucose detection. These coatings share features in common with GLP, and can be adapted for use with other types of sensors.

Assembly Means

The assembly means 14 couples the apparatus to a venous flow device 10 in a manner that brings the sensor 16 into contact with blood. The assembly means 14 has a sensor end 20 and an exterior face. The sensor end 20 refers to the portion of surface of the assembly means 14 that is enclosed when the assembly means 14 is coupled to a venous flow device 10. The sensor 16 is affixed to the sensor end 20 of the assembly means 14 and is positioned within the venous flow device 10 upon coupling of the assembly means 14 to a venous flow device 10.

In a typical embodiment, the assembly means 14 comprises a lure lock connector 18, of either the fixed or rotating variety. Variations on a lure lock 18, or a custom cap or housing can serve as an assembly means 14, providing a means for introducing the sensor 16 into the area of blood flow while protecting the integrity of the venous flow. The assembly means 14 can be designed to clip into place for secure and accurate positioning. A clip 70 can be used to attach and/or release the apparatus 14 to and from the venous flow device 10.

The assembly means 14 can be configured in a variety of ways, depending on the features of the venous flow device 10 to which it will be coupled, and on the desired positioning of the sensor 16 within the venous flow device 10. For example, it may be desirable to orient the sensor electrodes perpendicular, parallel, or at an angle with respect to the direction of blood flow. The assembly means 14 can include features that enhance security of the coupling to avoid inadvertent disconnection of the apparatus 14 from the venous flow device 10, or to avoid disruption of sensor function. A variety of exemplary embodiments of the assembly means 14 are depicted in FIGS. 1A-7C and 9A-10C.

In some embodiments of the apparatus, the assembly means 14 further comprises an alignment means 46 adapted to guide insertion of the sensor 16 into a venous flow device 10. For example, the alignment means 46 can comprise a needle having a lumen, or other piercing device. The piercing device 50 can be fixed or removable, and optionally, includes a slot 82 or other means to allow removal of the piercing device 50 without removing the sensor 16. The sensor shape can also be modified to facilitate removal of the piercing device 50 without disturbing the sensor 16 position.

Venous Flow Device

In some embodiments, the apparatus further comprises a venous flow device 10 coupled to the assembly means 14. The venous flow device 10 has a lumen 22 through which blood flows, and the sensor 16 is suspended within the lumen 22 of the venous flow device 10. The venous flow device 10 can be an intravenous catheter 90, such as a peripheral catheter, central catheter, or peripherally-inserted central catheter. In some embodiments, the venous flow device 10 comprises an external blood loop, such as is used in extra-corporeal membrane oxygenation or hemodialysis. The venous flow device 10 can have one or more lumens 22. The lumens can be in a coaxial or side-by-side arrangement. Optionally, an opening is provided between the lumens. An inter-lumenal opening can permit the introduction of a medication, such as an anticoagulant, into the area in which the sensor is suspended. Placement of the opening or openings can be designed to direct the medication or other agent to a particular portion or region of the sensor. In one embodiment, the assembly means 14 further comprises a side port 92 that provides a passage extending from the exterior of the assembly means to the lumen 22 of the venous flow device 10.

In some embodiments, the venous flow device 10 further comprises a septum 60 adapted to receive injections. For use with an external blood loop, the septum 60 can be affixed to a T-connector 12, for example, so that a sensor apparatus can be introduced into the external blood loop through the septum 60. In another embodiment, the external blood loop further comprises a cross connector 40 adapted to receive injections from opposing sides of the external blood loop, or to receive an assembly means 14 at one side and an alignment means 46 at the opposing side, which serves to guide the sensor 16 into place.

The apparatus can further comprise a medication delivery system, wherein the medication delivery system comprises means for infusing a medication into the venous flow device. In addition, the apparatus can include a feedback loop, wherein an output from the sensor is communicated to the medication delivery system. In such a closed loop system, sensor output can control infusion of medication, such as insulin and/or glucose, or other desired medication whose dosage would be adjusted on the basis of sensor-gathered information.

Monitors & Other Devices

In some embodiments, the sensor is operatively coupled to a monitor or other device. The coupling can be direct or telemetric, and facilitates continuous or regular monitoring of the subject's analyte levels. For example, in a hospital setting, the apparatus can be used to monitor a patient's glucose or other analyte level from a remote location, such as a nursing station.

In such an embodiment, the sensor communicates with a user interface as part of a sensing system. The sensing system may also include an auxiliary device. Examples of a user interface include, but are not limited to, a handheld device, such as a handheld computer, personal data assistant (PDA), telephone, remote control, and the like. A representative auxiliary device is a patient monitor. Representative sensing systems are described in U.S. patent application Ser. No. 10/899,623, filed Jul. 27, 2004, and entitled, "Sensing System with Auxiliary Display".

The sensor can be wired to a user interface, which is wired to an auxiliary device, such as a patient monitor. The sensor is typically a real-time sensor. The user interface may provide power to the sensor and/or the monitor may provide power to the sensor. Alternatively, the monitor recharges the user interface, which powers the sensor. The user interface may be detached from the patient monitor while the sensor is still powered and working. The user interface may transmit data wirelessly to the monitor. Alternatively, the glucose sensor may be wired to both a user interface and a patient monitor. The sensor may be powered by the user interface, monitor, or both.

The sensor electronics may include factory supplied reference values for a sensor. The factory supplied reference values may be stored in a nonvolatile memory, which can also be placed into a user interface for calibrating sensor signals. Reference values can be communicated to the sensor electronics or user interface directly from a blood glucose meter. The reference values can be downloaded to a personal computer or manually entered into a personal computer and then uploaded to the user interface and optionally sent to the sensor electronics. The reference values can be manually entered into the user interface and optionally sent to the sensor electronics.

The sensor electronics may include one or more of a sensor power supply, a regulator, a signal processor, a measurement processor, a measurement memory and a reference memory. The user interface may include one or more of a user interface power supply, a user interface processor, a reference memory, a measurement processor, a measurement memory, a signal processor, a regulator, and a mechanism for receiving data from an input device and/or sending data to an output device. Either or both of the user interface and sensor electronics can include a wireless communication mechanism.

Figure 11A:
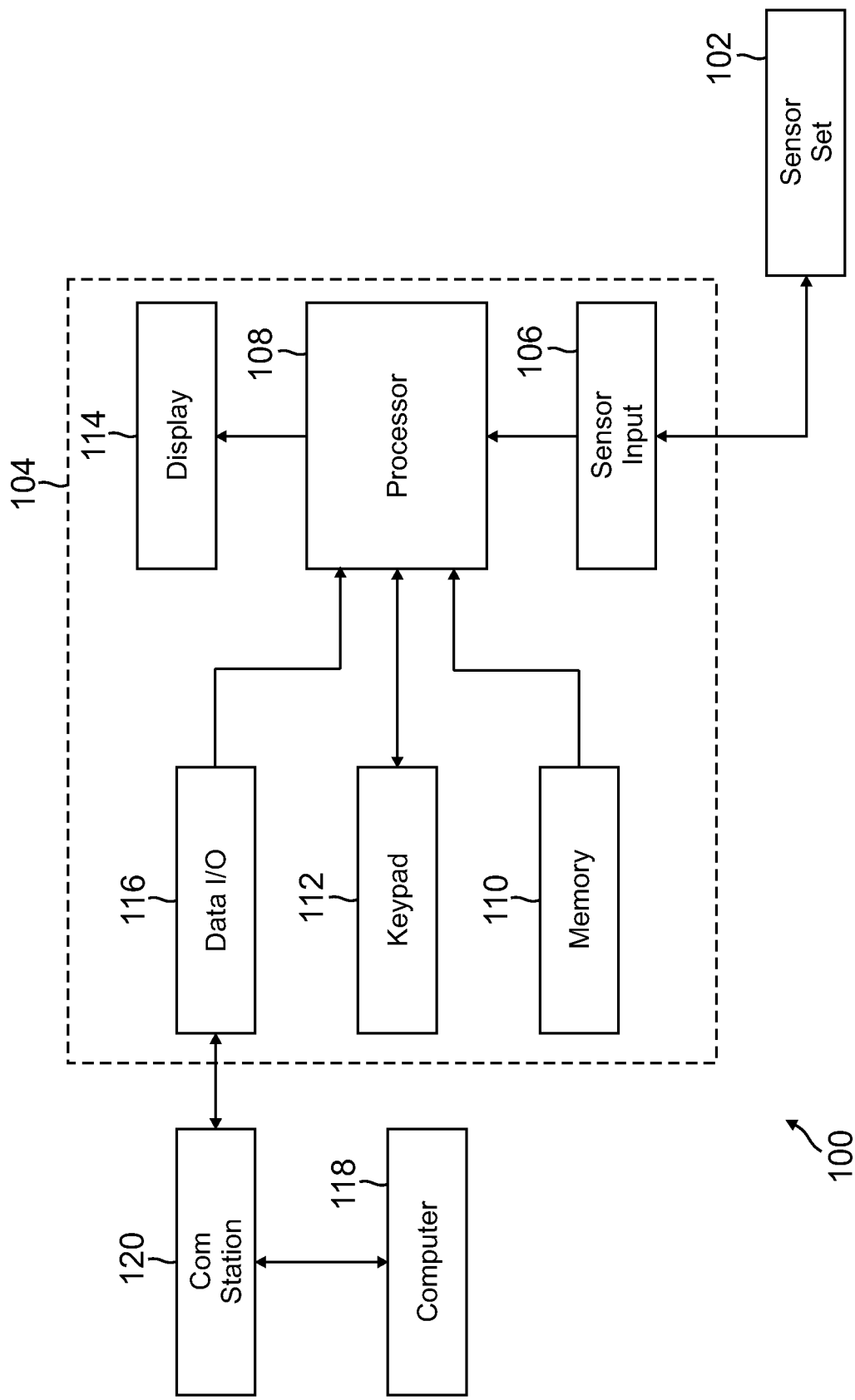
FIG. 11A is a block diagram of a characteristic monitor embodiment that can be used with the present invention.

FIG. 11A is a block diagram of a characteristic monitoring system 100 that can be used in accordance with an embodiment of the present invention. The characteristic monitoring system 100 generally includes a sensor set 102 that employs a sensor (as part of the apparatus of the invention) that produces a signal that corresponds to a measured characteristic of the user, such as a blood glucose level. The sensor set 102 communicates these signals to a characteristic monitor 104 that is designed to interpret these signals to produce a characteristic reading or value for the user, i.e. a measurement of the characteristic. The sensor signals enter the monitor 104 through a sensor input 106 and through the sensor input 106 the signals are conveyed to a processor 108. The processor 108 determines and manipulates the sensor readings within the monitor 104. The characteristic monitor 104 can provide additional functions that will aid in the treatment regime to which the characteristic reading applies. For example, the monitor may track meals, exercise and other activities that affect the treatment of diabetes. These additional functions can be combined with or independent from the characteristic readings determined by the monitor 104. Monitors of the invention have a number of embodiments and can for example be coupled to an infusion pump that can further provide a medication to a user.

Other components of the monitor 104 support the processor 108 in performing functions. A memory 110 is used to store data and instructions used by the processor 108. A data entry device 112 such as a keypad is used to receive direct input from the user and a display 114 such as a liquid crystal display (LCD), or the like, is used to relate information to the user. In addition, the monitor 104 includes a data port 116, such as a digital input/output (I/O) port.

The data port 116 can be used for the monitor 104 to communicate with a computer 118. To facilitate communication, the monitor 104 may interface with the computer 118 through a communication station 120 that can serve as a docking station for the monitor 104, for example. In some embodiments, the data port 116 within the monitor 104 can be directly connected to the computer 118. Through the communication link, data may be downloaded from the monitor 104, such as stored characteristic readings, settings, programs and other information related to the monitor's function. Thus, advanced analysis can be performed on the computer 118, freeing memory 110 within the monitor 104. Data such as characteristic readings, settings and programs can also be downloaded to the monitor 104. In this way, the monitor 104 can be conveniently reprogrammed without requiring tedious manual entry by the user.

Figure 11B:
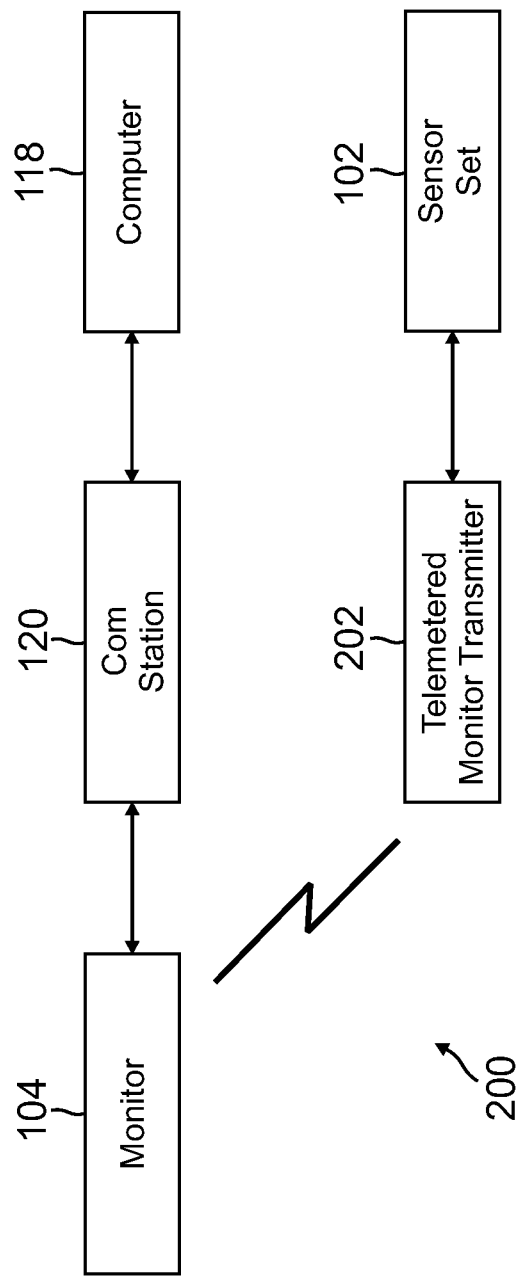
FIG. 11B is a block diagram of a telemetered characteristic monitor embodiment that can be used with the present invention.

FIG. 11B is a block diagram of a telemetered characteristic monitoring system embodiment of the invention. In this system embodiment 200, the sensor input 106 of the monitor 104 is a wireless receiver, such as a radio frequency (RF) receiver. The sensor set 102 provides a signal via wired link to a telemetered monitor transmitter 202, where the signal is interpreted and converted to an RF signal. The wireless receiver sensor input 106 of the monitor 104 converts the signal to data understandable to the monitor processor. With some advantages, the telemetered characteristic monitoring system can perform any or all the functions of the characteristic monitoring system of FIG. 11A.

A characteristic monitoring system 100, in accordance with a preferred embodiment of the present invention, includes a sensor set 102 and characteristic monitor device 104. The sensor set 102 generally utilizes an electrode-type sensor. However, in alternative embodiments, the system can use other types of sensors, such as electrically based sensors, chemically based sensors, optically based sensors, or the like. The sensor set 102 is connected to the monitor device 104 and provides a signal based upon the monitored characteristic (e.g., blood glucose). The characteristic monitor device 104 utilizes the received signal to determine the characteristic reading or value (e.g., a blood glucose level).

The telemetered characteristic monitor transmitter 202 generally includes the capability to transmit data. In alternative embodiments, the telemetered characteristic monitor transmitter 202 can include a receiver, or the like, to facilitate two-way communication between the sensor set 102 and the characteristic monitor 104. In alternative embodiments, the characteristic monitor 104 can be replaced with a data receiver, storage and/or transmitting device for later processing of the transmitted data or programming of the telemetered characteristic monitor transmitter 202. In addition, a relay or repeater can be used with a telemetered characteristic monitor transmitter 202 and a characteristic monitor 104 to increase the distance that the telemetered characteristic monitor transmitter 202 can be used with the characteristic monitor 104.

For example, a relay can be used to provide information to parents of children using the telemetered characteristic monitor transmitter 202 and the sensor set 102 from a distance. In a related embodiment, a relay can be used to provide information to medical professional and/or related caregiver regarding the physiological status of a user (e.g. a hypoglycemic event) in a situation where that event has not been acknowledged and/or addressed by the user within a specific time parameter (e.g. 15-45 minutes). In one illustrative embodiment, a physiological characteristic monitoring system includes a relay that automatically dials a predetermined telephone number as part of a notification scheme for an event that has not been acknowledged and/or addressed by the user. In further embodiments, the relay can include the capability to sound an alarm. In addition, the relay can be capable of providing telemetered characteristic monitor transmitter 202 data from the sensor set 102, as well as other data, to a remotely located individual via a modem connected to the relay for display on a monitor, pager or the like. The data can also be downloaded through the communication station 120 to a remotely located computer 118 such as a PC, laptop, or the like, over communication lines, by modem, wired or wireless connection. Wireless communication can include for example the reception of emitted radiation signals as occurs with the transmission of signals via RF telemetry, infrared transmissions, optical transmission, sonic and ultrasonic transmissions and the like. As disclosed herein, some embodiments of the invention can omit the communication station 120 and use a direct modem or wireless connection to the computer 118. In further embodiments, the telemetered characteristic monitor transmitter 202 transmits to an RF programmer, which acts as a relay, or shuttle, for data transmission between the sensor set 102 and a PC, laptop, communication station 118, a data processor, or the like. In further alternatives, the telemetered characteristic monitor transmitter 202 can transmit an alarm to a remotely located device, such as a communication station 118, modem or the like to summon help.

In addition, further embodiments can include the capability for simultaneous monitoring of multiple sensors and/or include a sensor for multiple measurements.

The characteristic monitor device 104 receives characteristic information, such as glucose data or the like, from the sensor set 102 and displays and/or logs the received glucose readings. Logged data can be downloaded from the characteristic monitor 104 to a PC, laptop, or the like, for detailed data analysis. In further embodiments, the characteristic monitoring system 100, 200 can be used in a hospital environment, or the like. For example, in a hospital environment, sensor information can be relayed to monitors in the patient room, to the nurses station, to the patients electronic medical records, and/or to a pump system which will use the information for closed-loop control of blood sugar levels. Still further embodiments of the present invention can include one or more buttons to record data and events for later analysis, correlation, or the like. Further buttons can include a sensor on/off button to conserve power and to assist in initializing the sensor set 102. The characteristic monitoring system 200 can also be employed with other medical devices to combine other patient data through a common data network system.

Further embodiments of the sensor set 102 can monitor the temperature of the sensor set 102, which can then be used to improve the calibration of the sensor. For example, for a glucose sensor, the enzyme reaction activity may have a known temperature coefficient. The relationship between temperature and enzyme activity can be used to adjust the sensor values to more accurately reflect the actual characteristic levels. In addition to temperature measurements, the oxygen saturation level can be determined by measuring signals from the various electrodes of the sensor set 102. Once obtained, the oxygen saturation level can be used in calibration of the sensor set 102 due to changes in the oxygen saturation levels and its effects on the chemical reactions in the sensor set 102. For example, as the oxygen level goes lower, the sensor sensitivity can be lowered. In alternative embodiments, temperature measurements can be used in conjunction with other readings to determine the required sensor calibration.

In preferred embodiments, the sensor set 102 facilitates accurate placement of a flexible thin film electrochemical sensor of the type used for monitoring specific blood parameters representative of a user's condition. Preferably, the sensor monitors glucose levels in the body, and can be used in conjunction with automated or semi-automated medication infusion devices of the external or implantable type as described in U.S. Pat. Nos. 4,562,751; 4,678,408; 4,685,903 or 4,573,994 (which are incorporated herein by reference), to control delivery of insulin to a diabetic patient. In addition, the monitor characteristic monitor 104 may typically be integrated into such a medication infusion device so that medication delivery and monitoring are conveniently provided within a single device.

Embodiments of the flexible electrochemical sensor can be constructed in accordance with thin film mask techniques to include elongated thin film conductors embedded or encased between layers of a selected insulative material, such as polyimide film or sheet, and membranes. The sensor electrodes at a tip end of the sensing portion are exposed through one of the insulative layers for direct contact with patient blood or other body fluids, when the sensing portion (or active portion) of the sensor is subcutaneously placed at an insertion site. The sensing portion is joined to a connection portion that terminates in conductive contact pads, or the like, which are also exposed through one of the insulative layers. In alternative embodiments, other types of implantable sensors, such as chemical based, optical based, or the like, can be used. Further description of flexible thin film sensors of this general type are be found in U.S. Pat. No. 5,391,250, entitled "METHOD OF FABRICATING THIN FILM SENSORS", which is herein incorporated by reference. The connection portion can be conveniently connected electrically to the monitor 104 or a telemetered characteristic monitor transmitter 202 by a connector block (or the like) as shown and described in U.S. Pat. No. 5,482,473, entitled "FLEX CIRCUIT CONNECTOR", which is also herein incorporated by reference. Thus, in accordance with embodiments of the present invention, subcutaneous sensor sets 102 are configured or formed to work with either a wired or a wireless characteristic monitoring system 100, 200.

Methods

The invention additionally provides a method of introducing a sensor into the circulating blood of a subject. The method comprises contacting a venous flow device with the circulating blood of the subject and introducing an apparatus of the invention into the venous flow device. The sensor contacts the circulating blood of the subject as the blood flows through the venous flow device. In one embodiment, the venous flow device comprises an external blood loop having a port adapted to receive the apparatus. Optionally, the external blood loop further comprises a second port adapted to receive an alignment means. The method can further comprise introducing an alignment means into the external blood loop from a side opposing the port adapted to receive the apparatus prior to introducing the apparatus.

In one embodiment, the method further comprises introducing an alignment means into the port prior to or simultaneously with introduction of the apparatus. The alignment means can be removed following introduction of the apparatus. Alternatively, the venous flow device can be a catheter.

In addition, embodiments of the invention provide a method for monitoring or detecting a biological substance in a subject. The biological substance may be glucose, lactate, amino acids or other analyte of interest. The method includes contacting an apparatus of the invention with blood or other tissue of the subject, and detecting the presence of the substance or analyte via the sensor. The method is particularly suited for subjects requiring repeated and/or continuous monitoring of an analyte, such as glucose for people with diabetes.

Also provided are methods for producing a sensor and apparatus as described herein. Such methods are readily accomplished using art accepted techniques. For example those of skill in the art can produce an illustrative embodiment of the method by generating an elongated conductive material having a protrudent end, the protrudent end comprising an electrode that detects the presence of an analyte; affixing a substrate to the conductive material; and coupling these elements to a support having an external surface, a proximal end, and a distal end; wherein the conductive material is positioned on the support and the protrudent end of the conductive material protrudes beyond the distal end of the support.

The foregoing description of preferred embodiments of the invention has been presented for the purposes of illustration and description. It is not intended to be exhaustive or to limit the invention to a precise form disclosed. Many modifications and variations are possible in light of the above teaching. It is intended that the scope of the invention be limited not by this detailed description, but rather by the claims appended hereto.

What is claimed is:

1. A method of detecting an analyte in a tissue of a subject comprising contacting the tissue of the subject with an apparatus comprising:
    an elongated conductive material having a protrudent end, the protrudent end comprising a sensor that detects the presence of an analyte, wherein the sensor comprises a plurality of layers including:
    a base layer;
    a plurality of electrodes disposed on the base layer;
    an analyte sensing layer disposed upon the electrode;
    an analyte modulating layer disposed on the analyte sensing layer; and
    a support having a proximal end and a distal end;
    wherein the conductive material is positioned on the support and the protrudent end of the conductive material comprising the sensor that detects the presence of an analyte:
    (a) protrudes beyond the distal end of the support; and
    (b) is positioned on the support in combination with a venous flow device and assembly means, wherein the sensor is affixed to a sensor end of the assembly means and the assembly means is adapted for coupling with the venous flow device.

2. The method of claim 1 wherein:
    the plurality of electrodes disposed on the base layer include a working electrode, a counter electrode, and a reference electrode,
    the analyte sensing layer comprises glucose oxidase; and
    the analyte sensing layer is disposed upon the working electrode.

3. The method of claim 1 wherein the support further comprises an intravenous infusion catheter having a lumen and an external surface.

4. The method of claim 3 wherein the protrudent end of the conductive material comprising the sensor that detects the presence of an analyte is positioned on the external surface of the intravenous infusion catheter.

5. The method of claim 1, wherein the venous flow device comprises an external blood loop.

6. The method of claim 5, wherein the external blood loop further comprises a septum adapted to receive injections.

7. The method of claim 1, wherein the sensor comprises a hydrophilic coating, wherein the coating swells and forms a gel upon contact with a wet environment.

8. The method of claim 7, wherein the coating achieves a swell volume upon contact with a wet environment that is of at least two times the thickness of the coating in a dry environment.

9. The method of claim 2, further comprising:
    a cover layer disposed on the analyte modulating layer and having an aperture, wherein the aperture is formed in the cover layer so as to expose the working electrode disposed at the distal end of the support to the tissue of the subject.

10. The method of claim 9, wherein the reference electrode is disposed on the support at a location relative to the aperture that is selected to avoid reference electrode exposure to the tissue of the subject.

11. The method of claim 1, wherein the sensor exhibits a flexibility that is sufficient to permit threading of the sensor through a venous flow device or a blood vessel.

12. The method of claim 1, further comprising an external coating disposed on the sensor, wherein the external coating comprises an anticoagulant, anti-inflammatory or antimicrobial agent.

13. A method of detecting an analyte in a tissue of a subject comprising:
    (i) contacting a venous flow device with a tissue of the subject; and
    (ii) coupling with the venous flow device an apparatus comprising:
        an elongated conductive material having a protrudent end, the protrudent end comprising a sensor that detects the presence of an analyte, wherein the sensor comprises a plurality of layers including:
        a base layer;
        an electrode disposed on the base layer;
        an analyte sensing layer; and
        a support having a proximal end and a distal end;
        wherein the conductive material is positioned on the support and the protrudent end of the conductive material comprising the sensor that detects the presence of an analyte:
        (a) protrudes beyond the distal end of the support; and
        (b) is positioned on the support in combination with the venous flow device and an assembly means, wherein the sensor is affixed to a sensor end of the assembly means and the assembly means is adapted for coupling with the venous flow device.

14. The method of claim 13 wherein the analyte is glucose, lactate or an amino acid.

15. The method of claim 13 wherein the tissue is circulating blood of the subject.

16. The method of claim 13 wherein the support further comprises an intravenous infusion catheter having a lumen and an external surface.

17. The method of claim 16 wherein the protrudent end of the conductive material comprising the sensor that detects the presence of an analyte is positioned on the external surface of the intravenous infusion catheter.

18. The method of claim 13, wherein the venous flow device comprises an external blood loop.

19. The method of claim 18, wherein the external blood loop further comprises a port adapted to receive an alignment means.

20. The method of claim 13, further comprising introducing an alignment means into the external blood loop from a side opposing the assembly means prior to coupling the apparatus with the venous flow device.

* * * * *